United States Patent [19]

Polson

[11] 3,989,818

[45] Nov. 2, 1976

[54] INFLUENZA VIRUS VACCINE

[75] Inventor: Alfred Polson, Milnerton, South Africa

[73] Assignee: South African Inventions Development Corporation, Pretoria, South Africa

[22] Filed: Oct. 4, 1974

[21] Appl. No.: 512,223

Related U.S. Application Data

[63] Continuation of Ser. No. 170,478, Aug. 10, 1971, abandoned.

[30] Foreign Application Priority Data

Aug. 14, 1970 South Africa.......................... 70/5633
Dec. 30, 1970 South Africa.......................... 70/8735

[52] U.S. Cl. .................................................. 424/89
[51] Int. Cl.² .......................................... A61K 39/18
[58] Field of Search ........................................ 424/89

[56] References Cited
UNITED STATES PATENTS 3,629,470   12/1971   Kanarek et al. ...................... 424/89

OTHER PUBLICATIONS

Albrecht ova et al. — Biologia Plantarum (Praha) vol. 12 No. 1 (1970) pp. 31–40.

Polson — Hemophilia (International Symposium (1968) pp. 77–82.

*Primary Examiner*—Sam Rosen
*Attorney, Agent, or Firm*—Millen, Raptes & White

[57] ABSTRACT

Influenza virus is purified, fractionated or concentrated in an aqueous medium, using a linear filamentary non-charged polymer, preferably polyethylene glycol, as an insolubilising agent, at a concentration not exceeding 5% by weight. Impurities and large virus particles can be fractionated off at PEG concentrations of say up to 1%. Phase separation is achieved most readily when assisted by ultra-centrifugation at low temperature between 0° and 6° C. Precipitation of the virus from dispersions of comparatively high concentration (say 600 HA units or more per ml.) results in intimately aggregated virus particles, which are easier to further purify, and which result in an improved vaccine. Novel concenrates of globular influenza virus are also described.

6 Claims, 1 Drawing Figure

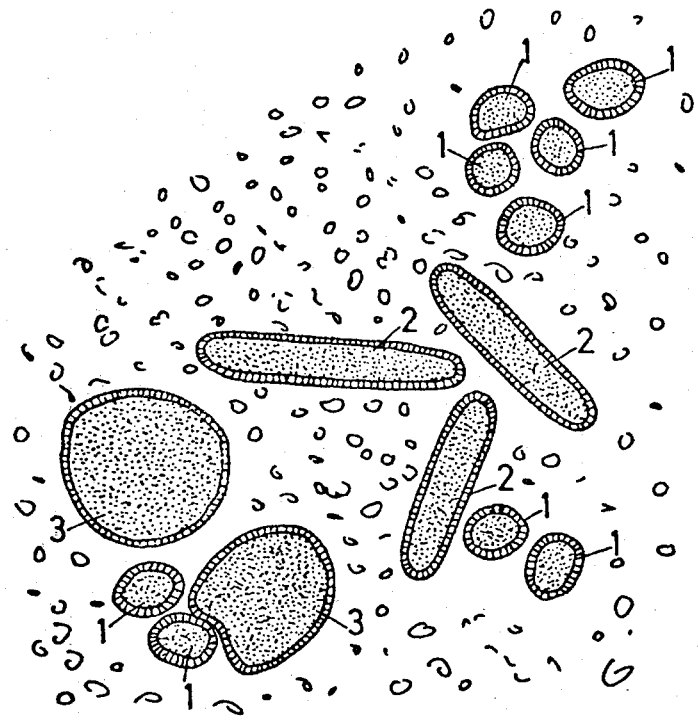

INFLUENZA VIRUS VACCINE

This is a continuation of application Ser. No 170,478, filed Aug. 10, 1971, now abandoned.

BACKGROUND OF THE INVENTION

The present invention relates to the purification and fractionation of the influenza type virus and certain new or improved virus products obtained thereby useful for example, for immunological purposes.

The invention will in the following be described with particular reference to human influenza virus, particularly of the so-called "Hong Kong" type. It is pointed out however, that certain animal influenza virus types, e.g. horse influenza are very similar and thus the invention may be extended to application to such very similar virus materials as well. Where particular strains are referred to in this specification such is done purely by way of illustrative example. Other strains of influenza virus could be used with substantially similar results.

In our British No. Nol 1006258 (U.S. Pat. No. 3 415 804) we described and claimed the fractionation and purification of proteinaceous substances including viruses, using polyethylene glycol as an insolubilising agent capable of preferentially bringing about the insolubilisation (e.g. precipitation) of certain protein species under conditions where certain other proteinaceous species are substantially left in solution.

The process has since then been used successfully for the fractionation, purification and concentration of a variety of viruses.

In accordance with British patent No. 1 226 743 for example, there is described and claimed the purification of certain viruses, including influenza viruses under a set of conditions which are considered the optimum conditions by the particular patentees. One of the preferred parameters described in that application, is the use of 7.5% polyethylene glycol (p.e.g.) for optimum precipitation of influenza virus.

We have now discovered that further and/or alternative advantages are attainable using different parameters. We have further found ways of producing virus products different from those normally produced, including vaccines having improved properties.

BRIEF SUMMARY OF THE INVENTION

In accordance with the invention there is provided a virus material treatment process which comprises subjecting influenza virus in a suitable aqueous medium to one or more insolubilising steps brought about by the presence in said aqueous medium of up to 5% by weight of polyethylene glycol, having a molecular weight between 3000 and 20000, the polyethylene glycol being replaceable by an amount equivalent in insolubilising power of another linear filamentary non-charged polymer, separating an insolubilised fraction from a non-insolubilised fraction and recovering virus material from one of said fractions.

In accordance with one aspect of the present invention, there is provided a process of purifying, fractionating or concentrating influenza virus which comprises subjecting the virus in a suitable aqueous medium to the insolubilising action of polyethylene glycol having a molecular weight between 3000 and 20000, preferably between 4000 and 8000, both inclusive, say 6000, employed at a concentration in said aqueous medium not exceeding 5% by weight, preferably not exceeding 4%, say between 3 and 4%, e.g. 3.5% by weight at a temperature not exceeding 35° C preferably not exceeding 25° C, at a pH between 6 and 9, preferably between 6 and 8, the ionic strength of the aqueous medium being below the salting out point for the virus, and the concentration of the virus in the aqueous medium prior to insolubilising corresponding at least to a haemagglutination titre of 1 in 32, being a serial twofold dilution of the starting material (equivalent to 320 HA units per ml), assuming more than 90%, say at least 95% of said titre being due to virus particles, bringing about phase separation of a virus fraction thus insolubilised out of said aqueous medium and removing such fraction from the residue aqueous medium.

The desired degree of precipitation is usually achieved substantially at polyethylene glycol (p.e.g.) concentrations not exceeding 3% by weight. However, we have observed that the precipitate becomes more rigid and is more easily handled if the concentration is raised slightly higher as defined above. This slightly higher concentration is nevertheless well below the concentration of 7.5% PEG previously recommended to achieve good recoveries. It is now found that raising the p.e.g. concentration above the limits now recommended may achieve little more but to precipitate the often minor and in any event frequently less desirable haemagglutinins. The formation of these haemagglutinins at the expense of the usually more desirable virus particles is preferably suppressed by processing as defined above the virus-bearing material immediately after its formation or at any rate, if prolonged storage is unavoidable, by storing the material at low temperature, preferably below 5° C but above freezing temperature. Surprisingly, it has been found that haemagglutinating activity as such is not a true measure of the immunogenicity of influenza antigen at all.

An important further advantage resides in the comparatively low viscosity which at 4% p.e.g. is less than half that at 7.5%. Moreover at higher p.e.g. concentrations the density of the medium approaches that of the precipitate. For both reasons centrifugation and separation at higher p.e.g. concentrations is much more difficult. These and other factors tend to increase the contamination of the product at higher p.e.g. concentrations.

In accordance with a modification of the above defined process, the polyethylene glycol may be partly or wholly replaced by another suitable polyalkylene glycol, dextran or another linear filamentary non-charged polymer in an amount equivalent in insolubilising power to the amount of polyethylene glycol thus replaced. By "suitable" in this context, we mean in particular that the amount required of substance for the insolubilisation, must not increase the viscosity of the aqueous medium at the prevailing temperature to a level where it becomes unduly difficult to carry out the process. Suitable substances are for example, polypropylene glycol or mixed polymers of ethylene glycol and higher homologues such as propylene glycol, dextran or poly 1, 4 dihydroxy butaneglycol. Preferably in all cases the molecular weight of the precipitant is within the range 3000 – 20000.

Dextran may be used advantageously for reprecipitating virus previously concentrated differently for further purification.

Examples of other linear filamentary non-charged polymers which, as confirmed by various experiments, can be used but are less preferred at present are nonylphenolethoxylate, polyvinyl alcohol and polyvinyl pyrrolidone.

The terms "precipitate" and "precipitant" are used in this specification in a colloquial sense.

When using a precipitant other than p.e.g. of H.wt 6000 the required amount, equivalent to a known required amount of p.e.g. 6000, may be calculated from the formula $$\beta = \frac{\overline{V}}{2.303}(1 + \frac{r_s}{r_r})^3 \qquad (1)$$

in which $\beta$ is inversely proportional to the concentration of polymer to be used,
$\overline{V}$ = partial specific volume of the polymer
$r_r$ = radius of the polymer molecule
$r_s$ = radius or Stokes radius of the virus particle.

On inspection of the equation, it would be clear that if $r_r$ be small, $\beta$ the slope of the precipitation curve would be greater, consequently complete separation would occur over a narrow range. This occurs with synthetic organic polymers. When $r_r$ is large, as with dextran, the slope ($\beta$) of the precipitation curve would be less and complete precipitation will occur over a wider range of dextran concentrations. As the excluded volume (which is a function of total length of the polymer molecules) of a thinner polymer is greater than that of a thicker polymer it stands to reason that the thin polymer will produce precipitation of the substance at a lower weight concentration than the polymer of greater diameter would do.

The relationship between required concentration and molecular weight of the precipitant is substantially linear in practice for most cases.

The process is preferably applied to suitable strains of so-called "Hong Kong Influenza." In such case it was for example found that 95% and more of the virus activity were precipitated from infected allantoic fluid, buffered to pH 7.1 with 0.066 M phosphate buffer using 2% p.e.g. of molecular weight 6000. Little or no further precipitation resulted from raising the concentration of p.e.g. to 3.5, though the precipitate was more easily handled. The residual 5% or less activity (determined in terms of HA activity) according to electron-microscopic observations could be ascribed largely or substantially wholly to small particles, apparently free HA particles of lesser immunological interest. The use of only 3.5% p.e.g. as compared with 7.5% as previously proposed results in a material saving with regard to reagents. The lower p.e.g. concentration may also assist in reducing the degree of contamination of the final product with p.e.g., where such contamination may be considered objectionable.

Phase separation may be assisted or brought about by centrifugation, preferably at a temperature between 0° to 6° C.

In preferred embodiments the virus particles are recovered in an intimately aggregated state to form a preferred and novel product. "Intimately aggregated" is intended to imply a condition in which appreciable numbers of the normal virus particles are "interlocked" to form strongly coherent clusters (as distinct from spontaneous loose viral aggregation), which are not broken up by non-drastic manners of redispersion. In fact, it is even possible to disrupt the individual particles of the intimate aggregate to release nucleic acids, whilst essentially retaining the aggregated state, e.g. ultrasonically or by shaking with ether for ½ – 3 hours in the cold (say at below 10° C, e.g. 4° C) or by forcing the virus through a narrow passage with pressure, thereby subjecting the virus to intensive accelerating and shear forces.

In accordance with one aspect of the present invention, this aggregation may be made positive use of e.g. when such aggregated virus, preferably in the form of killed virus, confers a better antigenic stimulus than the non-aggregated form, even though the total HA value of the aggregated virus material may appear to be less than that of the same amount of material in a non-aggregated form. An explanation of such an improved antigenic effect could be the release of antigenic particles at a slow rate after vaccination in a manner analogous to the liberation of antigen from an antigen system.

Thus, one aspect of the present invention provides, as a novel product a purified virus concentrate in which the, or a substantial portion of the virus particles are present in an intimately aggregated form, and wherein preferably the virus is killed for purposes of vaccination. The particles of the aggregate may be partly disrupted as aforesaid or not.

It is further considered an advantage of the aforesaid aggregated form of the virus that p.e.g. contamination may be reduced to a very low, more particularly negligible level without further complicated p.e.g. removal steps. The virus particles may readily be washed in the intimately aggregated state with a suitable washing liquor, e.g. a suitable aqueous buffer solution employed in a ratio of 1 part of concentrated virus precipitate to less than 50 parts of buffer solution at a time. Preferably, said ratio is less than 1:10, repeated several times.

In addition to the differential removal of p.e.g. by washing the method also ensures the removal of extraneous egg protein which co-precipitated with the influenza virus particles, when recovered from allantoic fluid, or the removal of other impurities, when the virus is grown in a different medium (several of which are known in the art).

If complete recovery of the virus antigen is desired by the differential removal of the contaminating p.e.g., the suspension of the precipitate may be cooled to approximately 0° and then mixed with 30% ethanol in saline at 31 20° and centrifuged. Under these conditions the virus precipitate is completely insoluble while the traces of contaminating p.e.g. dissolve in the ethanol-saline. This method is termed the cryoethanol procedure. A similar method for the removal of p.e.g. from protein fractions has been described by Polson et al. (1964).

Electron micrographs of the virus precipitates following an additional cryoethanol treatment indicate that approximately 10–15% of the virus particles had apparently lost the nucleo-proteins. It would appear that the monomeric and filamentous forms of the virus were more resistant to ethanol than the large or giant forms which seemed to have lost their nucleoproteins while the doughnut and filamentous forms appeared to be intact. The formation of the desirable aggregated state is assisted by carrying out the precipitating with PEG or the like from an aqueous dispersion containing more than 600 HA units, preferably more than 1000 HA units, more preferably more than 1500 HA units of virus particles per ml, these virus particles being determined with the virus essentially in the monomeric form.

On the other hand, if for any reason it is desirable for the virus material to be recovered in a non-aggregated or less aggregated state, such may be achieved by one or other manner of dissociation, e.g. ultrasonically. However, this should be done after the virus has been recovered in precipitated form.

A further aspect of the present invention provides for said insolubilisation with p.e.g. or its equivalent as defined above to be repeated more particularly after redispersion of the virus in a suitable aqueous medium. Preferably such repetition is carried out under conditions which again comply with the aforesaid parameters as defined for the process herein described further above. Preferably the volume of redispersion medium (aqueous) is less than the volume from which the virus was originally precipitated. In virus material thus reprecipitated we were unable to detect extraneous protein by examination in the electron microscope or by ultra-centrifugation. Furthermore, the final virus precipitate occupied a volume of approximately 0.1 ml as compared with the 200 ml volume of the infected allantoic fluid from which it had been derived, corresponding to a 2000-fold concentration increase and a purification factor approaching the 100% level.

In accordance with yet a further aspect of the present invention, there is provided a modification of the process outlined above which comprises subjecting an aqueous dispersion of influenza virus, e.g. Hong-Kong influenza virus to a preliminary precipitation with a polymer precipitant having a precipitating effect equivalent to that of polyethylene glycol having a molecular weight as previously defined and parameters other than p.e.g. concentration being also as previously defined, at a p.e.g. concentration in the aqueous medium not exceeding 1% by weight, preferably between 0.5 to 0.8%, say 0.6%, subjecting the resulting mixture to phase separation and separating as a fraction a phase enriched in proteinaceous material, (viral and/or non-viral), raising the p.e.g. concentration in the residual aqueous phase to a value at least 1% higher (based on the aqueous medium), said value preferably amounting to between 1.5% and 5%, more preferably between about 1.8 and 4.5% by weight, say substantially 3.5% by weight and recovering a further proteinaceous fraction by phase separation.

Again the invention provides for p.e.g. to be partly or wholly replaced by an equivalent amount of different polyalkylene glycol or other linear non-charged polymer as hereinbefore defined.

The proteinaceous fraction separated off at the lower p.e.g. concentration may be a waste product or a useful product. Thus, it has now been discovered that there may be present in influenza virus materials, more particularly certain strains of Hong-Kong influenza virus, pleomorphic forms of the virus. Thus it has now been observed that in addition to the normal "doughnut"-shaped particles there are present particles having a rod-shape about 5 to 50 or more times as long as the diameter of the more spherical normal particles and in addition particles which for the sake of convenience will be referred to as "giant globular particles" having a diameter several times that of the "doughnut" forms. Haemagglutinins may be seen around the peripheries and on the upper surfaces of these globular particles where they were observed to show up in the same regular manner as on the doughnut forms. The upper surfaces of these large particles were observed to be not smooth, but to have a dented appearance as if these giant particles are in the process of dissociation into the smaller particle variety. It was observed that by the modification of the process just described, it is possible to concentrate the giant globular particles and/or the rod-shaped particles in the fraction obtained at low p.e.g. concentration, and thus immediately in the next fraction to obtain a purified concentration of the smaller doughnut-shaped particles which may or may not be recovered in an aggregated form as described further above. These doughnut-shaped particles constitute an infective form of the virus.

In accordance with one proposal in accordance with the invention, these concentrates of the smaller particles, more particularly in the killed form, preferably aggregated, may be useful as an influenza vaccine of comparatively high specificity.

The other forms of the virus lack nucleic acid and are formed in comparatively large amounts if eggs are infected with large amounts of virus — and vice versa.

These large forms which are non-infective and pyrogenic can be isolated as aforesaid, dissociated and the resulting small particles may serve as an immunising material of low specificity. Such material as well as concentrates of the larger virus particles, and in particular the giant globular forms are considered novel products per se. The concentrate of giant globular particles and/or rod-shaped particles is likely initially to be contaminated with debris which may be separated out by different processes, e.g. by centrifugation or precipitation under different conditions, ion exchange etc.

Quite apart from the uses to which the different morphological forms of influenza virus may be put, the present process may be employed for the separation of the different morphological forms one from the other.

The giant globular form may also be separated out in different manners, for example by centrifugation alone or after the addition of polyethylene glycol which need not necessarily be employed in concentrations sufficient to bring about precipitation of the giant globular form in the absence of centrifugation. Such centrifugation may then be followed by subjecting the residual aqueous phase to further fractionation in accordance with the present invention.

A concentrate comprising both giant globular and rod-shaped particles may for example be further fractionated by centrifugation.

BRIEF DESCRIPTION OF THE DRAWING.

The drawing illustrates the appearance under the electron microscope of a precipitate obtained from virus-infected allantoic fluid with 0.6% PEG.

DETAILED DESCRIPTION OF PREFERRED EMBODIMENTS.

Various aspects of the present invention will be further illustrated in the following by way of example.

EXAMPLE 1

A Hong Kong strain of influenza virus A2/62 having a passage level in eggs of 46 was used. (A smaller number of passages is generally preferred.) 5 ml amounts of infected allantoic fluid were tested with p.e.g. (dissolved in 0.066 M phosphate buffer to pH 7.1) until a concentration of 2% p.e.g. was established. At that stage 95% of the activity had been precipitated. The p.e.g. concentration was raised to 4.0%. This did not have any appreciable effect on the yield but the precipitate became more rigid and easily handled. The precipitate which formed was removed by centrifugation at 1000 G. The HA content of the supernatant was determined and was found to have dropped from 640 to 32. This residual 5% HA activity was substantially ascribed to small free HA particles in view of electronmicroscopic observations. The precipitate was resuspended in 50 ml of the phosphate buffer and precipitation was repeated as before. Electronmicroscopic investigations of the precipitate showed the precipitate to be present in the form of dense intimately aggregated clusters of particles, substantially of the normal doughnut shape. P.e.g. contamination was negligible and no extraneous protein was detectable. The concentration factor was 2000. The experiment when repeated with X31 strains of virus gave the same results.

EXAMPLE 2

Example 1 is repeated. The aggregated virus is dissociated, by intense ultrasonic treatment. This can raise the HA titre to a value higher than the original. The virions are severely damaged.

EXAMPLE 3

Example 1 is repeated, the recovery of the allantoic fluid being followed immediately by p.e.g. precipitation as described. There was virtually no HA activity left in the supernatant at all.

EXAMPLE 4

Example 1 was repeated with the same strain of virus, however after only three passages. The allantoic fluid contained approximately 2000 HA units/ml about 95% of which was due to virus particles.

The procedure was modified by first raising the p.e.g. concentration to only 0.6% by weight and centrifuging off the small precipitate formed at 600 G with an ordinary commercial ultracentrifuge for 20 minutes. As shown diagrammatically in the accompanying drawing, the precipitate contains debris, some normal virus particles 1 of doughnut shape, an unusually high concentration of rod-shaped virus particles 2 and a newly discovered giant globular form 3 of the virus.

Further purification is possible by centrifugation (in order to remove debris and/or to separate the pleomorphic forms from one another).

Redispersion and precipitation with 0.6% p.e.g. will result in a further concentration of the rod-shaped and giant globular particles.

The giant globular particles may be separated from the rod-shaped particles by centrifugation.

The molecular weight of p.e.g. as referred to in this specification is to be understood as referring to the data as furnished by the major commercial suppliers. Thus, for example, where the present application refers to p.e.g. of molecular weight 6000 we used "Polyethylene Glycol 6000" as supplied by Shell. The code number is supposed to indicate the approximate molecular weight, although according to Shell's data sheet, the "average Molecular Weight Range" is 6000–7500 according to the method used by them. These variations of molecular weight are of little practical significance for the purposes of the present invention. Our own molecular weight determinations showed the p.e.g. used in most of the experiments to be almost entirely of molecular weight 6300.

Because of its ready commercial availability and favourable price, p.e.g. is at present preferred, at least for the first precipitation. Other, more expensive precipitants, e.g. dextran can be used for reprecipitation and further purification.

For an improved purification of the supernatant in a different batch, the centrifugation after the addition of 0.6% PEG was carried out for 20 min at between 1500 and 1900 G.

The PEG concentration in the supernatant was then raised to 4.0%. The precipitate which formed was separated off by centrifugation at 900–1200 G, and washed repeatedly with 3 volumes of aqueous buffer solution.

The washed virus when inspected under the electron microscope was found to be intimately aggregated, and redispersion would not cause the aggregated clusters to break up.

The following treatments were found to disrupt the individual particles sufficiently to release nucleic acids without loss of aggregation:

a. mild ultrasonic treatment;

b. shaking with ether at 4° C for between ½ hr and 3 hours (longer treatment, e.g. for 5 hours, resulted in dissociation of the aggregate);

c. forcing the material through a fine gap with sudden acceleration to 240 km/hr and high shear forces.

The product, both before and after partial disruption (and after inactivation of the virus with 0.1% formaldehyde) was useful as an influenza vaccine.

EXAMPLE 5

Thirty ml of allantoic fluid infected with the strain $A_2/8/68$ of Hong Kong virus was treated with 4% p.e.g. added as a 40% autoclaved solution and the precipitate obtained at 900–1200 × G for 60 minutes was resuspended in 2.0 ml of phosphate buffer solution to form what was termed "aggregated antigen (a)". An equal volume of the same pool of allantoic fluid was concentrated at 1200–1400 × G for 2 hours in the thin layer rotor to give a final concentrate diluted to 2.0 ml volume, forming the "monomeric antigen (b)". Both antigen preparations were held overnight at 4° C with 0.05% formaldehyde and the absence of infectious virus was confirmed, by failure to induce haemagglutinin formation in embryonated hen's eggs. Each antigen was inoculated into six guinea pigs respectively by a single 0.1 ml intramuscular injection. The results were as follows:

HA = haemagglutinin titre; H.A.I.pre. = titre in preimmunization serum; H.A.I. post. = titre in postimmunization serum.

| Experiment | State of Antigen | H.A. | H.A.I. pre | H.A.I. 3 weeks post mean | H.A.I. 7 weeks post mean |
|---|---|---|---|---|---|
| (a) | Aggregated | 3200 | <10 | 37.0 | 13.3 |
| (b) | Monomeric | 12000– | <10 | 12.5 | 6.6 |

-continued

| Experiment | State of Antigen | H.A. | H.A.I. pre | H.A.I. 3 weeks post mean | H.A.I. 7 weeks post mean |
|---|---|---|---|---|---|
| | | 25000 | | | |

Clearly the "aggregated" antigen produced a better response than the "monomeric" antigen.

It must be remembered that the "aggregated" antigen had been subjected to a series of further procedures as compared with the control monomeric antigen but that for the purpose of administering equivalent masses of antigenic material losses during such procedures were ignored.

EXAMPLE 6

X31 recombinant strain of influenza virus partly purified and concentrated by clarification, dialysis against five volumes of buffer overnight at 4° C, pervaporation in cellophane to one fifth volume and concentration in the thin layer rotor with a wash cycle, was divided into equal portions.

i. One portion received no treatment other than 0.1% formaldehyde inactivation. This formed monomeric antigen (a).

ii. Another portion was diluted eight-fold with phosphate buffer solution and precipitated with 4% p.e.g. added as a powder, centrifuged from supernatant (900–1200 × G for 60 min) resuspended in phosphate buffer and centrifuged as before; the final deposit being resuspended in phosphate buffer to the original starting volume of this second portion. After 0.1% formaldehyde inactivation this formed aggregated antigen (b).

In this experiment each guinea pig was inoculated with 1.0 ml of a ½ dilution of antigen. It will be seen that all experimental animals received equal amounts of virus antigen as calculated on the basis of equivalent dilutions of the common starting material (assuming no losses).

RESULTS:

| State of Antigen | H.A. | H.A.I. pre mean | H.A.I. 3 weeks post inoc. mean | H.A.I. 7 weeks post inoc. mean |
|---|---|---|---|---|
| (a) Monomeric | 1600 | <10 | 40 | 30 |
| (b) Aggregated | 400 | <10 | 50 | 27 |

In Examples 5 and 6 the thin layer centrifugation was carried out with a rotor as described in Polson, A. and Stannard, L. M. Concentration of viruses at low rotor velocities. Virology, 40, (1970), 781–791.

EXAMPLE 7

Hong Kong virus $A_2 8/68$ and influenza virus X31 were precipitated from solutiions of different virus concentrations, each time with 3.5% PEG 6000. After centrifugation as in previous examples, the aggregation of the virus particles was inspected with the following result: The "intimate aggregation" as herein defined was strongest for samples precipitated from solutions containing at least 1500 HA units of virus per ml. It diminished only slightly when concentrations were reduced to 1000 HA units per ml. Above 600 HA units per ml the greater part of the virus precipitate was intimately aggregated. Below 320 HA units per ml the precipitate was substantially non-aggregated.

It was previously assumed that a high ratio of PEG (or the like) to virus was unavoidable for the attainment of good yields. This wrong assumption was based at least in part on the assumption now also shown wrong that the HA titre constitutes a reliable measure of the immunological effectiveness of an influenza vaccine, even if this titre results, to a considerable extent, from haemagglutinins, represented by comparatively small, difficulty precipitable virus fragments. A high PEG concentration is a disadvantage from a cost point of view and, as shown above, makes the effective phase separation more difficult due to an increased viscosity and the decreased difference in density between the virus precipitate and the supernatant. Quite generally, the removal of residual PEG becomes more difficult.

The known process which was furthermore carried out by precipitation from comparatively dilute virus solutions (a further factor leading to a high ratio of PEG to virus in the process) resulted in a loose virus precipitate in which the virus particles were present essentially as individual particles, at the most weakly held together. Because this in turn resulted in a comparatively high HA titre, this form of the virus precipitate was considered essential for a hih effectiveness of vaccines produced therefrom. It was therefore surprising that strongly and intimately aggregated virus particles have now been shown to result in a vaccine of improved immunising power which moreover is much more easily purified and handled.

What we claim is:

1. In an influenza vaccine comprising influenza virus particles in an immunologically effective and physiologically tolerated form and amount, the improvement wherein said influenza vaccine consists essentially of influenza virus particles in the form of intimately aggregated virus particles interlocked as strong, coherent clusters distinguishable from spontaneous loose viral aggregations by:

a. not being dispersable to the monomeric virus state without causing disruption of the individual virus particles, such that the individual virus particles in said clusters can be disrupted to release nucleic acids therefrom while essentially retaining the coherent cluster state;

b. said clusters exhibiting a reduced hemaglutinin content in comparison with the same amount of monomeric virus particles; and c. said clusters being capable of preparation from an aqueous dispersion of monomeric influenza virus particles having a pH of 6–9 and containing more than 600 HA units of virus particles per ml., only HA units ascribable to actual influenza virus particles being taken into account, by
  i. precipitating said virus from said aqueous dispersion at a temperature not exceeding 35° C. by adding 3–4% by weight polyethylene glycol having a molecular weight of about 6,000–7,000 thereto;
  ii. separating an insolubilized fraction consisting essentially of said strong, coherent influenza virus clusters by phase separation from a non-insolubilized fraction; and
  iii. preparing said vaccine from said clusters.

2. An influenza vaccine according to claim 1, further characterized by being free of extraneous protein detectable either by electron microscope examination or by ultracentrifugation.

3. An influenza vaccine according to claim 2, wherein the influenza virus particles are dead.

4. An influenza vaccine according to claim 1, wherein the aggregated influenza virus particles are partially disrupted by the release of nucleic acids therefrom in such a manner that the coherent cluster state is substantially preserved.

5. Influenza virus particles in the form of intimately aggregated virus particles interlocked as strong, coherent clusters distinguishable from spontaneous loose viral aggregations by:

a. not being dispersable to the monomeric virus state without causing disruption of the individual virus particles, such that the individual virus particles in said clusters can be disrupted to release nucleic acids therefrom while essentially retaining the coherent cluster state;

b. said clusters exhibiting a reduced hemaglutinin content in comparison with the same amount of monomeric virus particles; and c. said clusters being capable of preparation from an aqueous dispersion of monomeric influenza virus particles having a pH of 6–9 and contaiing more than 600 HA units of virus particles per ml., only HA units ascribable to actual influenza virus particles being taken into account, by
  i. precipitating said virus from said aqueous dispersion at a temperature not exceeding 35° C. by adding 3–4% by weight polyethylene glycol having a molecular weight of about 6,000–7,000 thereto; and
  ii. separating an insolubilized fraction consisting essentially of said strong, coherent influenza virus clusters by phase separation from a non-insolubilized fraction.

6. Influenza virus particles according to claim 5, wherein the aggregated influenza virus particles are partially disrupted by the release of nucleic acids therefrom in such a manner that the aggregated cluster state is substantially preserved.

* * * * *